(12) United States Patent
Porat et al.

(10) Patent No.: US 6,720,709 B2
(45) Date of Patent: Apr. 13, 2004

(54) PIEZOELECTRIC TRANSDUCER

(75) Inventors: Yarlv Porat, Halfa (IL); Yoseph Tsaliah, Klryat Blallk (IL); Eyal Doron, Kiryat Yam (IL)

(73) Assignee: Remon Medical Technologies Ltd., Caesavea (IL)

( * ) Notice: Subject to any disclaimer, the term of this patent is extended or adjusted under 35 U.S.C. 154(b) by 0 days.

(21) Appl. No.: 10/235,968

(22) Filed: Sep. 6, 2002

(65) Prior Publication Data

US 2003/0006673 A1 Jan. 9, 2003

Related U.S. Application Data

(63) Continuation of application No. 09/691,887, filed on Oct. 20, 2000, now Pat. No. 6,504,286, which is a continuation of application No. 09/000,553, filed on Dec. 30, 1997, now Pat. No. 6,140,740.

(51) Int. Cl.$^7$ .............................................. H01L 41/08
(52) U.S. Cl. ....................................................... 310/324
(58) Field of Search ................................. 310/311, 322, 310/324, 334, 337, 357–359, 800, 366, 330, 316.01, 317, 319

(56) References Cited

U.S. PATENT DOCUMENTS

| | | | | |
|---|---|---|---|---|
| 2,967,957 A | * | 1/1961 | Massa | 310/324 X |
| 4,056,742 A | * | 11/1977 | Tibbetts | 310/357 |
| 4,064,375 A | * | 12/1977 | Russell et al. | 381/190 |
| 4,170,742 A | * | 10/1979 | Itagaki et al. | 310/324 |
| 4,433,400 A | * | 2/1984 | DeReggi et al. | 367/163 |
| 4,517,665 A | * | 5/1985 | DeReggi et al. | 367/163 |
| 4,558,249 A | * | 12/1985 | Lerch et al. | 310/322 |
| 4,653,036 A | * | 3/1987 | Harris et al. | 310/800 X |
| 4,835,435 A | * | 5/1989 | Yeung et al. | 310/324 |
| 5,160,870 A | * | 11/1992 | Carson et al. | 310/339 |
| 5,339,290 A | * | 8/1994 | Greenstein | 367/163 |
| 5,381,067 A | * | 1/1995 | Greenstein et al. | 310/334 |
| 5,381,386 A | * | 1/1995 | Lum et al. | 367/163 |
| 5,495,137 A | * | 2/1996 | Park et al. | 310/331 |
| 5,757,104 A | * | 5/1998 | Getman et al. | 310/317 |

* cited by examiner

Primary Examiner—Mark Budd
(74) Attorney, Agent, or Firm—G.E. Ehrlich (1995) Ltd.

(57) ABSTRACT

A miniature piezoelectric transducer element is provided, comprising: (a) a cell element having a cavity; (b) a flexible piezoelectric layer attached to the cell member, the piezoelectric layer having an external surface and an internal surface, the piezoelectric layer featuring such dimensions so as to enable fluctuations thereof at its resonance frequency upon impinging of an external acoustic wave; and (c) a first electrode attached to the external surface and a second electrode attached to the internal surface of the piezoelectric layer. At least one of the electrodes may be specifically shaped so as to provide a maximal electrical output, wherein the electrical output may be current, voltage or power. A preferred shape of the electrodes includes two cores interconnected by a connecting member. The transducer element may function as a transmitter. When used as a transmitter, the electrodes are electrically connected to an electrical circuit including a switching element for modulating the reflected acoustic wave by controllably changing the mechanical impedance of the piezoelectric layer according to the frequency of an electrical message signal arriving from an electronic member, such as a sensor. Third and fourth electrodes may be attached to the piezoelectric layer and the electrical circuit, such that the switching element alternately connects the electrodes in parallel and anti-parallel electrical connections so as to controllably change the mechanical impedance of the piezoelectric layer.

16 Claims, 7 Drawing Sheets

PIEZOELECTRIC TRANSDUCER

This is a continuation of U.S. patent application Ser. No. 09/691,887, filed Oct. 20, 2000, now U.S. Pat. No. 6,504, 286 which is a continuation of U.S. patent application Ser. No. 09/000,553, filed Dec. 30, 1997, now U.S. Pat. No. 6,140,740, issued Oct. 31, 2000.

FIELD AND BACKGROUND OF THE INVENTION

The present invention relates to an acoustic transducer and, in particular, to a miniature flexural piezoelectric transducer for receiving acoustic energy transmitted from a remote source and converting such energy into electrical power for activating an electronic circuit. Further, the present invention relates to a miniature flexural piezoelectric transmitter for transmitting acoustic information by modulating the reflection of an external impinging acoustic wave.

The prior art provides various examples of piezoelectric transducers. Examples of such piezoelectric transducers are disclosed in U.S. Pat. Nos. 3,792,204; 4,793, 825; 3,894, 198; 3,798,473, and 4,600,855.

However, none of the prior art references provides a miniature flexural piezoelectric transducer specifically tailored so as to allow the usage of low frequency acoustic signals for vibrating the piezoelectric layer at its resonant frequency, wherein substantially low frequency signals herein refer to signals having a wavelength that is much larger than the dimensions of the transducer. Further, none of the prior art references provides a miniature transducer having electrodes specifically shaped so as to maximize the electrical output of the transducer. Further, none of the above references provides a transducer element which may be integrally manufactured with any combination of electronic circuits by using photolithographic and microelectronics technologies.

Further, the prior art fails to provide a miniature flexural piezoelectric transmitter which modulates the reflected acoustic wave by controllably changing the mechanical impedance of the piezoelectric layer according to a message signal received from an electronic component such as a sensor. Further, the prior art fails to provide such transmitter wherein the piezoelectric layer is electrically connected to a switching element, the switching element for alternately changing the electrical connections of the transmitter so as to alternately change the mechanical impedance of the piezoelectric layer. Further, the prior art fails to provide such transducer wherein the mechanical impedance of the piezoelectric layer is controlled by providing a plurality of electrodes attached thereto, the electrodes being electrically interconnected in parallel and anti-parallel electrical connections. Further, the prior art fails to provide such transmitter wherein the piezoelectric layer features different polarities at distinct portions thereof. Further, the prior art fails to provide such transmitter which includes a chamber containing a low pressure gas for enabling asymmetrical fluctuations of the piezoelectric layer. Further, the prior art fails to provide such transmitter having two-ply piezoelectric layer.

SUMMARY OF THE INVENTION

The present invention is of a miniature flexural transducer element, comprising: (a) a cell element having a cavity; (b) a substantially flexible piezoelectric layer attached to the cell member, the piezoelectric layer having an external surface and an internal surface, the piezoelectric layer featuring such dimensions so as to enable fluctuations thereof at its resonance frequency upon impinging of an external acoustic wave; and (c) a first electrode attached to the external surface and a second electrode attached to the internal surface of the piezoelectric layer. Preferably, the cavity is etched into a substrate including an electrically insulating layer and an electrically conducting layer. The first electrode is preferably integrally made with a substantially thin electrically conducting layer, the electrically conducting layer being disposed on the substrate and connected thereto by a sealing connection. The cell member may be circular or hexagonal in cross section. According to further features in preferred embodiments of the invention described below, the substrate may include a plurality of cell members electrically connected in parallel or serial connections. Preferably, at least one of the electrodes is specifically shaped so as to provide a maximal electrical output, wherein the electrical output may be current, voltage or power. A preferred shape of the electrodes includes two cores interconnected by a connecting member. A transducer element according to the present invention may also be used as a transmitter.

Preferably, the cavity of the transducer element includes gas of low pressure so as to allow its usage as a transmitter. According to the present invention there is further provided a transmitter element, comprising: (a) a cell element having a cavity; (b) a substantially flexible piezoelectric layer attached to the cell member, the piezoelectric layer having an external surface and an internal surface, the piezoelectric layer featuring such dimensions so as to enable fluctuations thereof at its resonance frequency upon impinging of an external acoustic wave; and (c) a first electrode attached to the external surface and a second electrode attached to the internal surface of the piezoelectric layer, the electrodes being electrically connected to an electrical circuit including a switching element for controllably changing the mechanical impedance of the piezoelectric layer. Preferably, the switching frequency of the switching element equals the frequency of an electrical message signal arriving from an electronic member, such as a sensor, thereby modulating a reflected acoustic wave according to the frequency of the message signal. The transmitter element may include a third electrode attached to the external surface and a fourth electrode attached to the internal surface of the piezoelectric layer. When using such a configuration, the switching element preferably alternately connects the electrodes in parallel and anti-parallel, thereby controllably changing the mechanical impedance of the piezoelectric layer. According to a specific configuration, the electrodes are interconnected by means of a built-in anti-parallel electrical connection. Alternatively, the electrodes may be interconnected by means of a built-in parallel electrical connection. The switching element may be an on/off switch. According to another embodiment, the piezoelectric layer includes first and second portions having opposite polarities. According to yet another embodiment, the transmitter element may include two cell members electrically interconnected by means of a built-in parallel or anti-parallel electrical connection. Alternatively, the switching element may alternately connect the cell members in parallel and anti-parallel electrical connections. The cell members may have piezoelectric layers of opposite polarities. According to yet another embodiment, the cavity of the transmitter element is covered by a two-ply piezoelectric layer including an upper layer bonded to a lower layer. The upper and lower layers may feature opposite polarities. The upper and lower layers may be separated by an insulating layer disposed therebetween. Further according to the present invention there is provided a method of transmitting acoustic information, comprising: (a) providing a substantially flexible piezoelectric layer having first and second electrodes attached thereto, the piezoelectric layer being attached to a cell member, the electrodes being electrical connected to an electrical circuit including a switching element; (b) providing an acoustic wave for impinging on the piezoelectric layer, the acoustic wave having a reflected portion; (c) modulating the reflected portion of the acoustic wave by controlling the mechanical impedance of the piezoelectric layer, said controlling by switching the switching element at a frequency which equals the frequency of a message signal arriving from an electronic component such as a sensor. The method may further comprise: (a) providing third and fourth electrodes attached to the piezoelectric layer, the third and fourth electrodes being electrically connected to the electrical circuit; (b) changing the electrical connections between the electrodes by means of the switching element so as to change the mechanical impedance of the piezoelectric layer. According to a specific configuration, the first and second electrodes are attached to a first cell member and the third and fourth electrodes are attached to a second cell member.

The present invention successfully addresses the shortcomings of the presently known configurations by providing a miniature flexural piezoelectric transducer specifically tailored so as to allow the usage of low frequency acoustic signals for vibrating the piezoelectric layer at its resonant frequency, wherein substantially low frequency signals herein refer to signals having a wavelength that is much larger than dimensions of the transducer. Further, the present invention addresses the shortcomings of the presently known configurations by providing such transducer element having electrodes specifically shaped so as to maximize the electrical output of the transducer, and which may be integrally manufactured with any combination of electronic circuits by using photolithographic and microelectronics technologies.

Further, the present invention addresses the shortcomings of the presently known configurations by providing a miniature flexural piezoelectric transmitter which modulates a reflected acoustic wave by controllably changing the mechanical impedance of the piezoelectric layer according to a message signal received from an electronic component such as a sensor. Further, the present invention addresses the shortcomings of the presently known configurations by providing such transmitter wherein the mechanical impedance of the piezoelectric layer is controlled by providing a plurality of electrodes attached thereto, the electrodes being interconnected in parallel and anti-parallel electrical connections, and wherein at least a portion of the electrodes is electrically connected to a switching element, the switching element for alternately changing the electrical connections between the electrodes so as to alternately change the mechanical impedance of the piezoelectric layer.

BRIEF DESCRIPTION OF THE DRAWINGS

The invention is herein described, by way of example only, with reference to the accompanying drawings, wherein:

FIG. 2a is a cross section of a transducer element according to the present invention taken along line C—C in FIG. 1a;

FIG. 2b is a cross section of a transducer element according to the present invention taken along line D—D in FIG. 1a;

FIG. 2c is a cross section of a transducer element according to the present invention taken along line E—E in FIG. 1a;

FIG. 2d is a cross section of a transducer element according to the present invention taken along line F—F in FIG. 1a;

FIG. 2e is a cross section of a transducer element according to the present invention taken along line G—G in FIG. 1a;

DESCRIPTION OF THE PREFERRED EMBODIMENTS

Figure 1A:
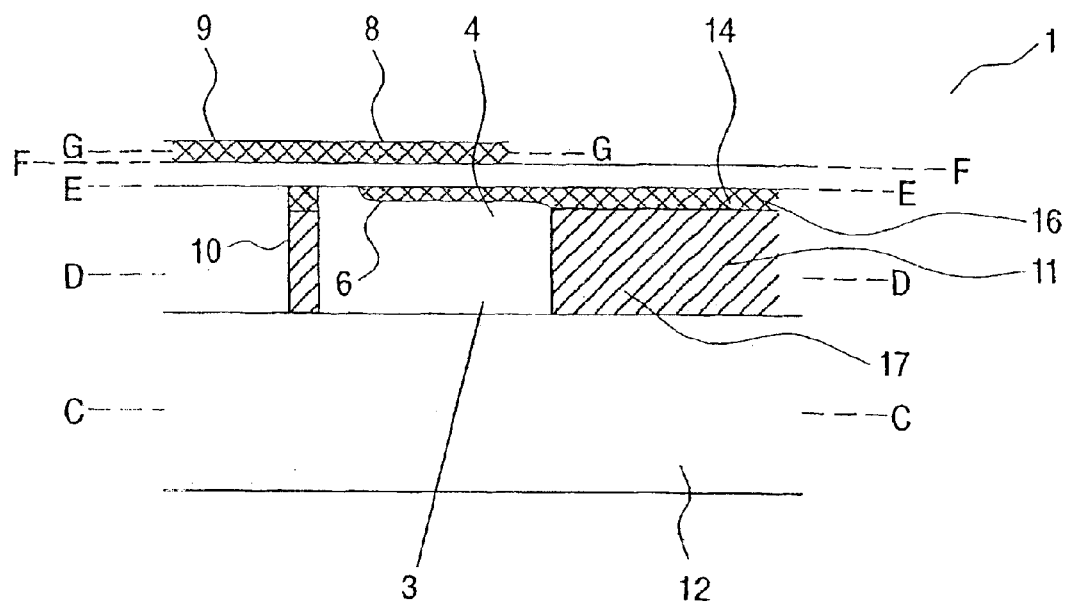
FIG. 1a is a longitudinal section of a transducer element according to the present invention taken along lines A—A in FIGS. 2a–2e.

The present invention is of a miniature flexural piezoelectric transducer for receiving acoustic energy transmitted from a remote acoustic radiation source and converting such energy into electrical power for activating an electronic circuit.

Further, the present invention is of a transmitting element and method for transmitting information by modulating the reflection of an external impinging acoustic wave arrived from a remote transmitter.

The principles and operation of a transducer element according to the present invention may be better understood with reference to the drawings and the accompanying description.

Referring now to the drawings, FIGS. 1a, 1b and 2a–2e illustrate a preferred embodiment of a transducer element according to the present invention. As shown in the figures, the transducer element 1 includes at least one cell member 3 including a cavity 4 etched into a substrate and covered by a substantially flexible piezoelectric layer 2. Attached to piezoelectric layer 2 are an upper electrode 8 and a lower electrode 6, the electrodes for connection to an electronic circuit.

The substrate is preferably made of an electrical conducting layer 11 disposed on an electrically insulating layer 12, such that cavity 4 is etched substantially through the thickness of electrically conducting layer 11.

Electrically conducting layer 11 is preferably made of copper and insulating layer 12 is preferably made of a polymer such as polyimide. Conventional copper-plated polymer laminate such as Kapton™ sheets may be used for the production of transducer element 1. Commercially available laminates such as Novaclad™ may be used. Alternatively, the substrate may include a silicon layer, or any other suitable material. Alternatively, layer 11 is made of a non-conductive material such as Pyralin™.

Preferably, cavity 4 is etched into the substrate by using conventional printed-circuit photolithography methods. Alternatively, cavity 4 may be etched into the substrate by using VLSI/micro-machining technology or any other suitable technology.

Piezoelectric layer 2 may be made of PVDF or a copolymer thereof. Alternatively, piezoelectric layer 2 is made of a substantially flexible piezoceramic. Preferably, piezoelectric layer 2 is a poled PVDF sheet having a thickness of about 9–28 $\mu$m.

Preferably, the thickness and radius of flexible layer 2, as well as the pressure within cavity 4, are specifically selected so as to provide a predetermined resonant frequency. When using the embodiment of FIGS. 1a and 1b, the radius of layer 2 is defined by the radius of cavity 4.

By using a substantially flexible piezoelectric layer 2, the present invention allows to provide a miniature transducer element whose resonant frequency is such that the acoustic wavelength is much larger than the extent of the transducer. This enables the transducer to be omnidirectional even at resonance, and further allows the use of relatively low frequency acoustic signals which do not suffer from significant attenuation in the surrounding medium.

Prior art designs of miniature transducers, however, rely on rigid piezoceramic usually operating in thickness mode. In such cases the resonant frequency relates to the size of the element and speed of sound in the piezoceramic, and is higher by several orders of magnitude.

The present invention provides a transducer which is omnidirectional, i.e., insensitive to the direction of the impinging acoustic rays, thereby substantially simplifying the transducer's operation relative to other resonant devices. Such a transducer element is thus suitable for application in confined or hidden locations, where the orientation of the transducer element cannot be ascertained in advance.

According to a specific embodiment, cavity 4 features a circular or hexagonal shape with radius of about 200 $\mu$m. Electrically conducting layer 11 preferably has a thickness of about 15 $\mu$m. Cell member 3 is preferably etched completely through the thickness of electrically conducting layer 11. Electrically insulating layer 12 preferably features a thickness of about 50 $\mu$m. The precise dimensions of the various elements of a transducer element according to the present invention may be specifically tailored according to the requirements of the specific application.

Cavity 4 preferably includes a gas such as air. The pressure of gas within cavity 4 may be specifically selected so as to predetermine the sensitivity and ruggedness of the transducer as well as the resonant frequency of layer 2.

Figure 2A:
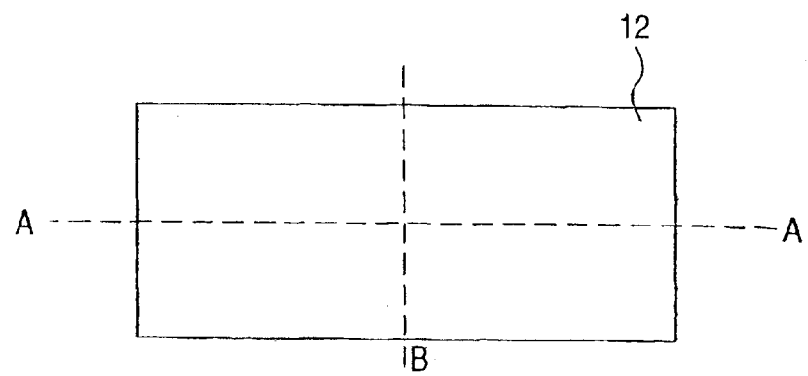
Figure 2B:
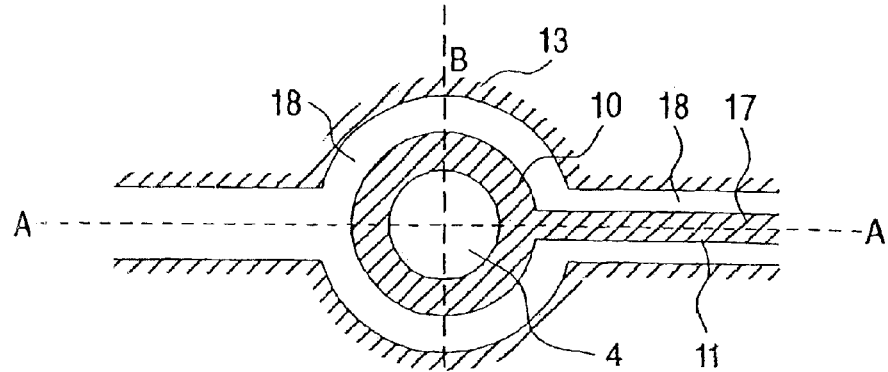

As shown in FIG. 2b, an insulating chamber 18 is etched into the substrate, preferably through the thickness of conducting layer 11, so as to insulate the transducer element from other portions of the substrate which may include other electrical components such as other transducer elements etched into the substrate. According to a specific embodiment, the width of insulating chamber 18 is about 100 $\mu$m. As shown, insulating chamber 18 is etched into the substrate so as to form a wall 10 of a predetermined thickness enclosing cavity 4, and a conducting line 17 integrally made with wall 10 for connecting the transducer element to another electronic component preferably etched into the same substrate, or to an external electronic circuit.

Figure 1B:
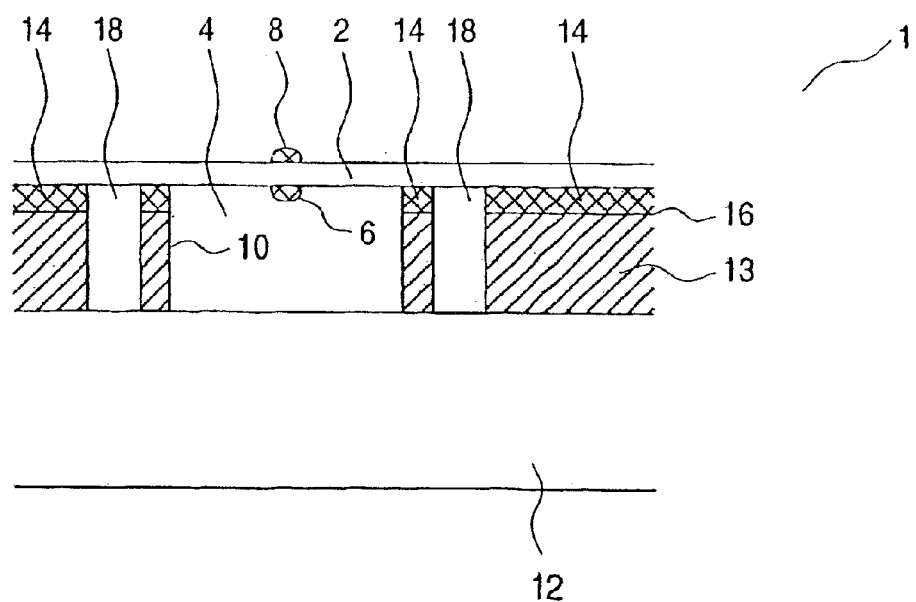
FIG. 1b is a longitudinal section of a transducer element according to the present invention taken along lines B—B in FIGS. 2a–2e.
Figure 2C:
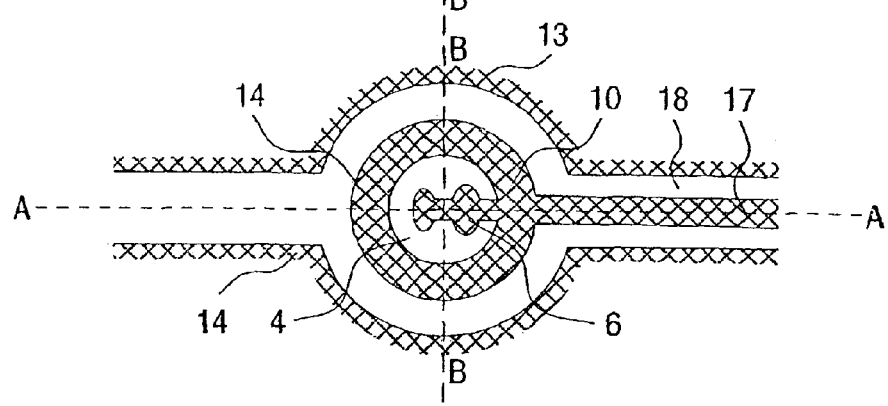
Figure 2D:
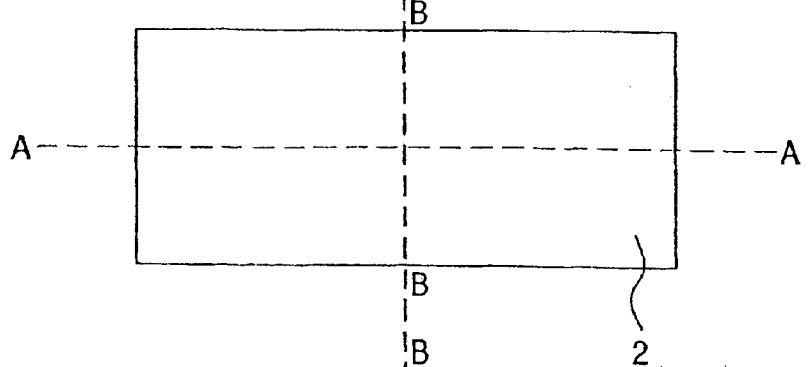
Figure 2E:
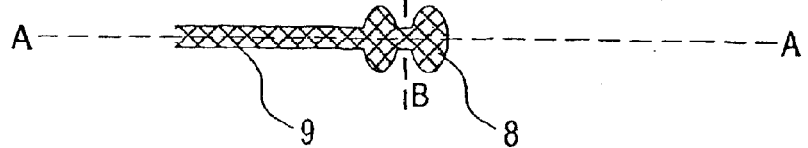

As shown in FIGS. 1a and 1b, attached to piezoelectric layer 2 are upper electrode 8 and lower electrode 6. As shown in FIGS. 2c and 2e, upper electrode 8 and lower electrode 6 are preferably precisely shaped so as to cover a predetermined area of piezoelectric layer 2. Electrodes 6 and 8 may be deposited on the upper and lower surfaces of piezoelectric membrane 2, respectively, by using various methods such as vacuum deposition, mask etching, painting, and the like.

As shown in FIG. 1a, lower electrode 6 is preferably made as an integral part of a substantially thin electrically conducting layer 14 disposed on electrically conducting layer 11. Preferably, electrically conducting layer 14 is made of a Nickel-Copper alloy and is attached to electrically conducting layer 11 by means of a sealing connection 16. Sealing connection 16 may be made of indium. According to a preferred configuration, sealing connection 16 may feature a thickness of about 10 $\mu$m, such that the overall height of wall 10 of cavity 4 is about 20–25 $\mu$m.

As shown in FIG. 2c, electrically conducting layer 14 covers the various portions of conducting layer 11, including wall 10 and conducting line 17. The portion of conducting layer 14 covering conducting line 17 is for connection to an electronic component such as a neighboring cell.

According to a preferred embodiment of the present invention, electrodes 6 and 8 are specifically shaped to include the most energy-productive region of piezoelectric layer 2 so as to provide maximal response of the transducer while optimizing the electrode area, and therefore the cell capacitance, thereby maximizing a selected parameter such as voltage sensitivity, current sensitivity, or power sensitivity of the transducer element.

The vertical displacement of piezoelectric layer 2, $\Psi$, resulting from a monochromatic excitation at angular frequency $\omega$ is modeled using the standard equation for thin plates:

$$(\nabla^2 - \gamma^2)(\nabla^2 + \gamma^2)\Psi - \frac{3(1-v^2)}{2Qh^3}P + \frac{3iZ\omega(1-v^2)}{2Qh^3}\Psi = 0$$

wherein Q is the Young's modulus representing the elasticity of layer 2; h the half-thickness of layer 2; v is the Poisson ratio for layer 2; $\gamma$ is the effective wavenumber in the layer given by: $\gamma^4 = 3\rho(1-v^2)\omega^2/Qh^2$, wherein $\rho$ is the density of layer 2 and $\omega$ is the angular frequency of the applied pressure (wherein the applied pressure may include the acoustic pressure, the static pressure differential across layer 2 and any other pressure the transducer comes across); Z is the mechanical impedance resulting from the coupling of layer 2 to both external and internal media of cavity 4, wherein the internal medium is preferably air and the external medium is preferably fluid; P is the acoustic pressure applied to layer 2, and $\overline{\Psi}$ represents the average vertical displacement of layer 2.

When chamber 4 is circular, the solution (given for a single frequency component $\omega$) representing the dynamic displacement of a circular layer 2 having a predetermined radius a, expressed in polar coordinates, is:

$$\Psi(r,\varphi) = \frac{I_1(\gamma a)[J_0(\gamma r) - J_0(\gamma a)] + J_1(\gamma a)[I_0(\gamma r) - I_0(\gamma a)]}{2h\rho\omega^2 L_0(\gamma a) + i\omega Z L_2(\gamma a)} P$$

$$L_0(z) = I_0(z)J_1(z) + J_0(z)I_1(z), \; L_2(z) = J_2(z)I_1(z) - I_2(z)J_1(z)$$

$$Z = \frac{P_A}{i\omega H_A} + i\left[\frac{4}{3\pi} + \frac{1}{6}\right]\omega \rho_W a$$

wherein:

$\Psi(r,\phi)$ is time-dependent and represents the displacement of a selected point located on circular layer 2, the specific location of which is given by radius r and angle $\phi$;

J and I are the normal and modified Bessel functions of the first kind, respectively; $P_A$, $H_A$ are the air pressure within cavity 4 and the height of chamber 4, respectively; and $\rho_W$ is the density of the fluid external to cavity 4.

The first term of the impedance Z relates to the stiffness resulting from compression of air within cavity 4, and the second term of Z relates to the mass added by the fluid boundary layer. An additional term of the impedance Z relating to the radiated acoustic energy is substantially negligible in this example.

The charge collected between electrodes 6 and 8 per unit area is obtained by evaluating the strains in layer 2 resulting from the displacements, and multiplying by the pertinent off-diagonal elements of the piezoelectric strain coefficient tensor, $e_{31}$, $e_{32}$, as follows:

$$Q(r, \varphi, t) = e_{31}\left(\frac{\partial \Psi}{\partial x}\right)^2 + e_{32}\left(\frac{\partial \Psi}{\partial y}\right)^2$$

wherein:

$Q(r,\phi,t)$ represents the charge density at a selected point located on circular layer 2, the specific location of which is given by radius r and angle $\phi$;

x is the stretch direction of piezoelectric layer 2; y is the transverse direction (the direction perpendicular to the stretch direction) of layer 2;

$e_{31}$, $e_{32}$ are off-diagonal elements of the piezoelectric strain coefficient tensor representing the charge accumulated at a selected point on layer 2 due to a given strain along the x and y directions, respectively, which coefficients being substantially dissimilar when using a PVDF layer.

$\Psi$ is the displacement of layer 2, taken as the sum of the displacement for a given acoustic pressure P at frequency f, and the static displacement resulting from the pressure differential between the interior and exterior of cavity 4, which displacements being extractable from the equations given above.

The total charge accumulated between electrodes 6 and 8 is obtained by integrating $Q(r,\phi,t)$ over the entire area S of the electrode:

$$Q = \int_S Q(r, \varphi, t) d^{\rho}x$$

The capacitance C of piezoelectric layer 2 is given by:

$$C = \frac{\varepsilon}{2h} \int_S d^{\rho}x,$$

wherein $\in$ is the dielectric constant of piezoelectric layer 2; and $2h$ is the thickness of piezoelectric layer 2.

Accordingly, the voltage, current and power responses of piezoelectric layer 2 are evaluated as follows:

$$V = \frac{2h \int_S Q(r, \varphi, t) d^{\rho}x}{\varepsilon \int_S d^{\rho}x},$$

$$I = 2i\omega \int_S Q(r, \varphi, t) d^{\rho}x,$$

$$W = \frac{4ih\left[\int_S Q(r, \varphi, t) d^{\rho}x\right]^2}{\varepsilon \int_S d^{\rho}x}$$

The DC components of Q are usually removed prior to the evaluation, since the DC currents are usually filtered out. The values of Q given above represent peak values of the AC components of Q, and should be modified accordingly so as to obtain other required values such as RMS values.

According to the above, the electrical output of the transducer expressed in terms of voltage, current and power responses depend on the AC components of Q, and on the shape S of the electrodes. Further, as can be seen from the above equations, the voltage response of the transducer may be substantially maximized by minimizing the area of the electrode. The current response, however, may be substantially maximized by maximizing the area of the electrode.

Figure 3:
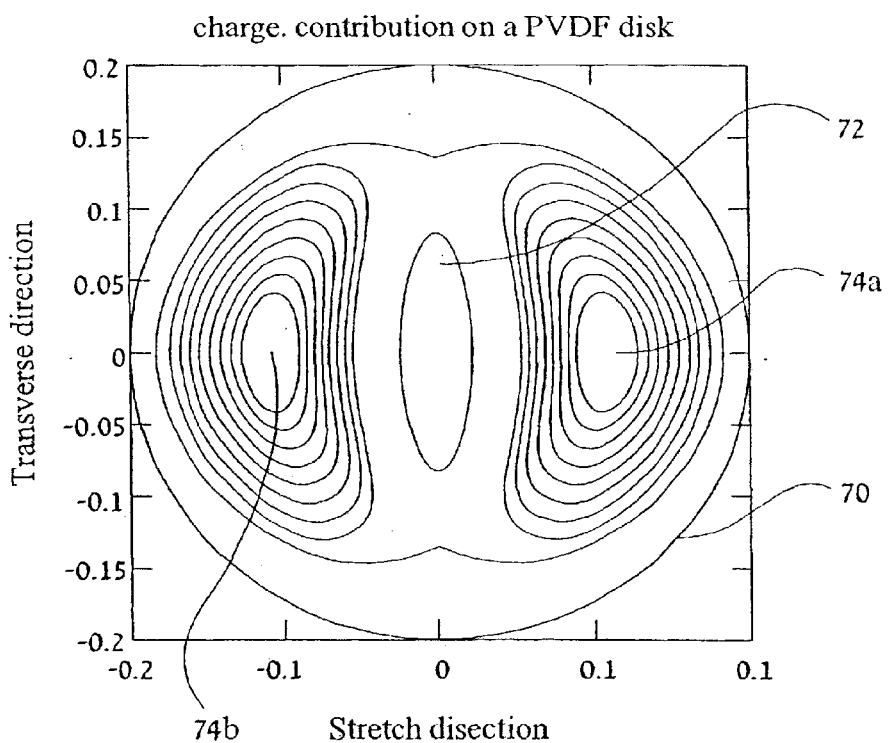
FIG. 3 shows the distribution of charge density across a piezoelectric layer of a transducer element resulting from the application of a constant pressure over the entire surface of the layer.

FIG. 3 shows the distribution of charge density on a circular piezoelectric layer 2 obtained as a result of pressure (acoustic and hydrostatic) applied uniformly over the entire area of layer 2, wherein specific locations on layer 2 are herein defined by using Cartesian coordinates including the stretch direction (x direction) and the transverse direction (y direction) of layer 2. It can be seen that distinct locations on layer 2 contribute differently to the charge density. The charge density vanishes at the external periphery 70 and at the center 72 of layer 2 due to minimal deformation of these portions. The charge density is maximal at two cores 74a and 74b located symmetrically on each side of center 72 due to maximal strains (in the stretch direction) of these portions.

A preferred strategy for optimizing the electrical responses of the transducer is to shape the electrode by selecting the areas contributing at least a selected threshold percentage of the maximal charge density, wherein the threshold value is the parameter to be optimized. A threshold value of 0% relates to an electrode covering the entire area of layer 2.

Figure 4:
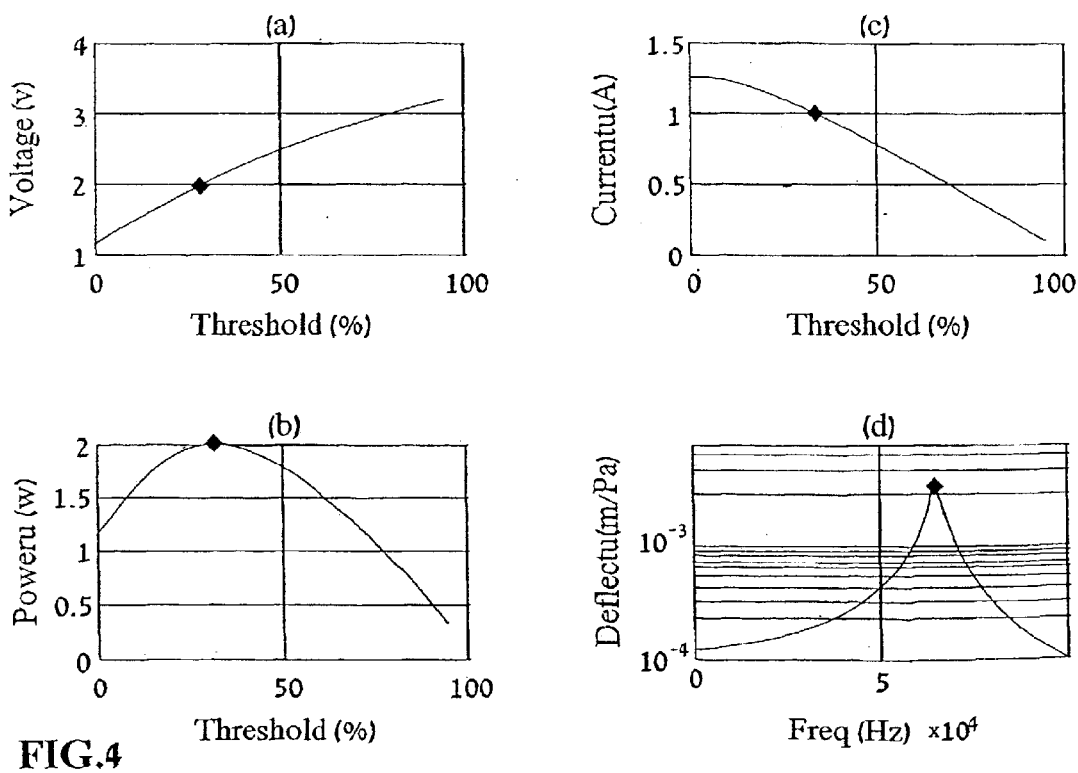
FIG. 4 shows the results of optimization performed for the power response of a transducer according to the present invention.

FIG. 4 shows the results of an optimization performed for the power response of a transducer having a layer 2 of a predetermined area. As shown in the figure, the threshold value which provides an optimal power response is about 30% (graph b). Accordingly, an electrode which covers only the portions of layer 2 contributing at least 30% of the maximal charge density yields a maximal power response. The pertinent voltage response obtained by such an electrode is higher by a factor of 2 relative to an electrode completely covering layer 2 (graph a). The current response obtained by such electrode is slightly lower relative to an electrode completely covering layer 2 (graph c). Further as shown in the figure, the deflection of layer 2 is maximal when applying an acoustic signal at the resonant frequency of layer 2 (graph d).

Figure 5:
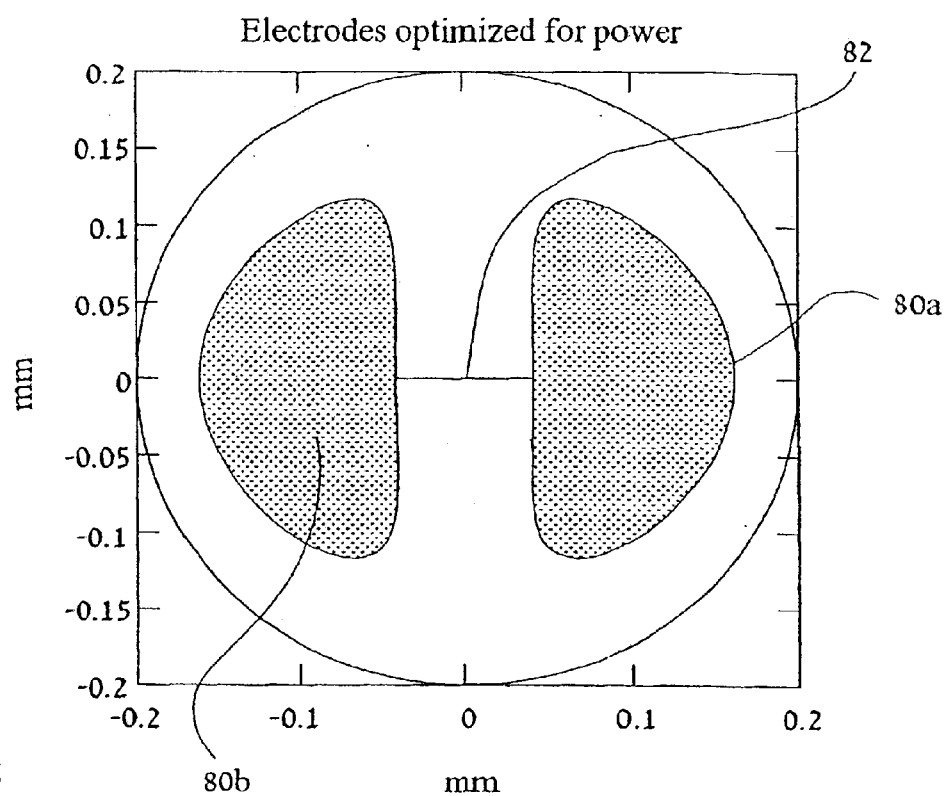
FIG. 5 shows a preferred electrode shape for maximizing the power response of a transducer according to the present invention.

A preferred electrode shape for maximizing the power response of the transducer is shown in FIG. 5, wherein the electrode includes two electrode portions 80a and 80b substantially covering the maximal charge density portions of layer 2, the electrode portions being interconnected by means of a connecting member 82 having a minimal area.

Preferably, portions 80a and 80b cover the portions of layer 2 which yield at least a selected threshold (e.g. 30%) of the maximal charge density.

According to the present invention any other parameter may be optimized so as to determine the shape of electrodes 6 and 8. According to further features of the present invention, only one electrode (upper electrode 8 or lower electrode 6) may be shaped so as to provide maximal electrical response of the transducer, with the other electrode covering the entire area of layer 2. Since the charge is collected only at the portions of layer 2 received between upper electrode 8 and lower electrode 6, such configuration is operatively equivalent to a configuration including two shaped electrodes having identical shapes.

Figure 6:
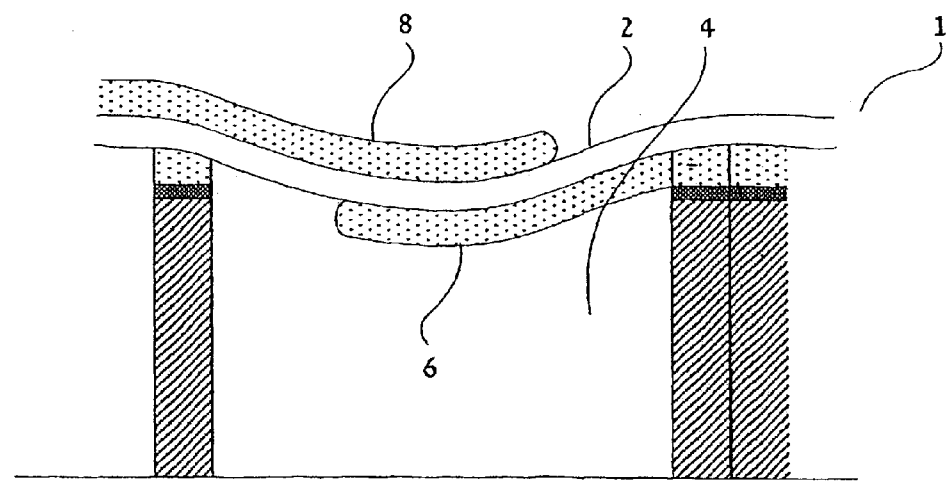
FIG. 6 is a longitudinal section of another embodiment of a transducer element according to the present invention capable of functioning as a transmitter.

Referring now to FIG. 6, according to another embodiment of the present invention chamber 4 of transducer element 1 may contain gas of substantially low pressure, thereby conferring a substantially concave shape to piezoelectric membrane 2 at equilibrium. Such configuration enables to further increase the electrical response of the transducer by increasing the total charge obtained for a given displacement of layer 2. The total displacement in such an embodiment is given by: $\Psi = P_0 \Psi_{DC} + P\Psi_{AC} \cos \omega t$, wherein $P_0$ is the static pressure differential between the exterior and the interior of cavity 4; $\Psi_{DC}$ is the displacement resulting from $P_0$; P is the amplitude of the acoustic pressure; and $\Psi_{DC}$ the displacement resulting from P.

Accordingly, the strain along the x direction includes three terms as follows:

$$S_{xx} = \left(\frac{\partial \Psi}{\partial x}\right)^2 = P_0^2 \left(\frac{\partial \Psi_{DC}}{\partial x}\right)^2 + P^2 \left(\frac{\partial \Psi_{AC}}{\partial x}\right)^2 \cos^2 \omega t + 2P_0 P \frac{\partial \Psi_{DC}}{\partial x} \frac{\partial \Psi_{AC}}{\partial x} \cos \omega t$$

wherein the DC component is usually filtered out.

Thus, by decreasing the pressure of the medium (preferably air) within cavity 4 relative to the pressure of the external medium (preferably fluid), the value of $P_0$ is increased, thereby increasing the value of the third term of the above equation.

Such embodiment of the present invention makes it possible to increase the charge output of layer 2 for a given displacement, thereby increasing the voltage, current and power responses of the transducer without having to increase the acoustic pressure P. Further, such embodiment enables to further miniaturize the transducer since the same electrical response may obtain for smaller acoustic deflections. Such embodiment is substantially more robust mechanically and therefore more durable than the embodiment shown in FIGS. 1a and 1b. Such further miniaturization of the transducer enables to use higher resonance frequencies relative to the embodiment shown in FIGS. 1a and 1b.

Preferably, a transducer element 1 according to the present invention is fabricated by using technologies which are in wide use in the microelectronics industry so as to allow integration thereof with other conventional electronic components. When the transducer element includes a substrate such as Copper-polymer laminate or silicon, a variety of conventional electronic components may be fabricated onto the same substrate.

According to the present invention, a plurality of cavities 4 may be etched into a single substrate 12 and covered by a single piezoelectric layer 2 so as to provide a transducer element including a matrix of transducing cells members 3, thereby providing a larger energy collecting area of predetermined dimensions while still retaining the advantage of miniature individual transducing cell members 3. When using such configuration, the transducing cell members 3 may be electrically interconnected in parallel or serial connections, or combinations thereof, so as to tailor the voltage and current response of the transducer. Parallel connections are preferably used so as to increase the current output while serial connections are preferably used so as to increase the voltage output of the transducer.

Further, piezoelectric layer 2 may be completely depolarized and then repolarized at specific regions thereof so as to provide a predetermined polarity to each of the transducing cell members 3. Such configuration enables to reduce the complexity of interconnections between the cell members 3.

A transducer element according to the present invention may be further used as a transmitter for transmitting information to a remote receiver by modulating the reflection of an external impinging acoustic wave arrived from a remote transmitter.

Referring to FIG. 6, the transducer element shown may function as a transmitter element due to the asymmetric fluctuations of piezoelectric layer 2 with respect to positive and negative transient acoustic pressures obtained as a result of the pressure differential between the interior and exterior of cavity 4.

A transmitter element according to the present invention preferably modulates the reflection of an external impinging acoustic wave by means of a switching element connected thereto. The switching element encodes the information that is to be transmitted, such as the output of a sensor, thereby frequency modulating a reflected acoustic wave.

Such configuration requires very little expenditure of energy from the transmitting module itself, since the acoustic wave that is received is externally generated, such that the only energy required for transmission is the energy of modulation.

Specifically, the reflected acoustic signal is modulated by switching the switching element according to the frequency of a message electric signal arriving from another electronic component such as a sensor, so as to controllably change the mechanical impedance of layer 2 according to the frequency of the message signal.

Preferably, the invention uses a specific array of electrodes connected to a single cell member 3 or alternatively to a plurality of cell members so as to control the mechanical impedance of layer 2.

Figure 7A:
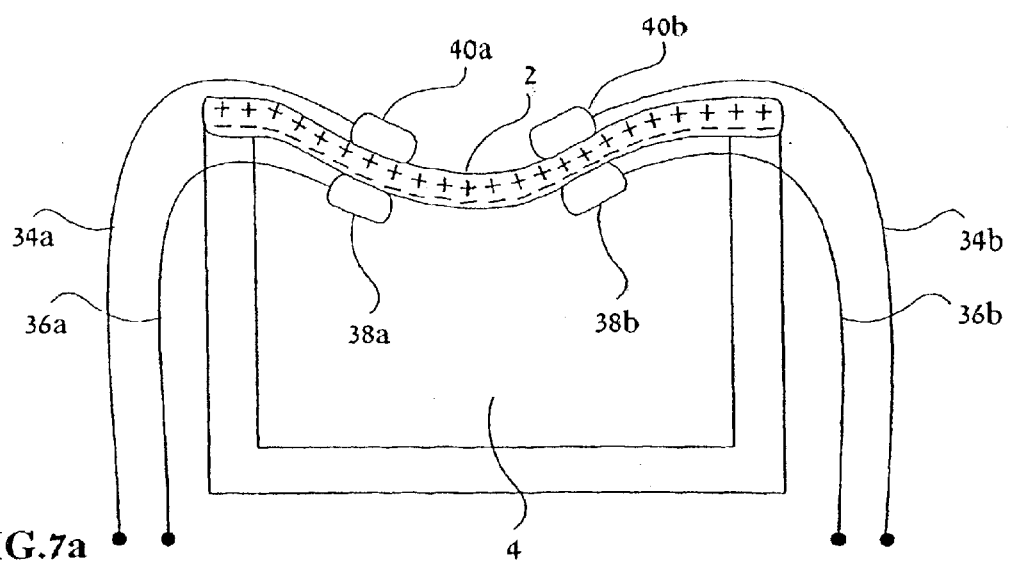
FIGS. 7a–7f are schematic views of possible configurations of transmitters according to the present invention including parallel and anti-parallel electrical connections for controllably changing the mechanical impedance of the piezoelectric layer.
Figure 7B:
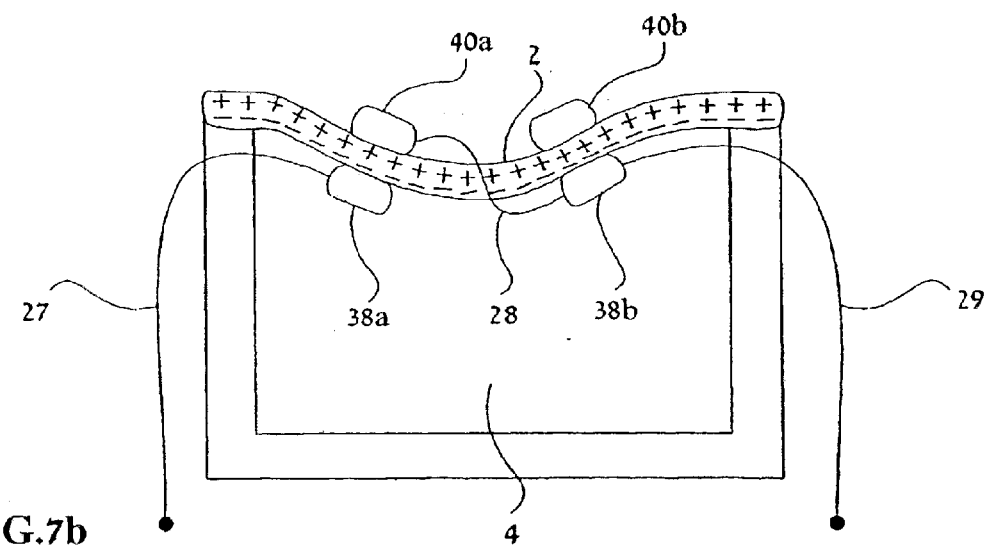

FIGS. 7a–7g illustrate possible configurations for controllably change the impedance of layer 2 of a transmitter element. Referring to FIG. 7a, a transmitter element according to the present invention may include a first and second pairs of electrodes, the first pair including an upper electrode 40a and a lower electrode 38a, and the second pair including an upper electrode 40b and a lower electrode 38b. Electrodes 38a, 38b, 40a and 40b are electrically connected to an electrical circuit by means of conducting lines 36a, 36b, 34a and 34b, respectively, the electrical circuit including a switching element (not shown) so as to alternately change the electrical connections of conducting lines 36a, 36b, 34a and 34b.

Preferably, the switching element switches between a parallel connection and an anti-parallel connection of the electrodes. A parallel connection decreases the mechanical impedance of layer 2, wherein an anti-parallel connection increases the mechanical impedance of layer 2. An anti-parallel connection may be obtained by interconnecting line 34a to 36b and line 34b to 36a. A parallel connection may be obtained by connecting line 34a to 34b and line 36a to 36b. Preferably, the switching frequency equals the frequency of a message signal arriving from an electrical component such as a sensor.

According to another embodiment (FIG. 7b), upper electrode 40a is connected to lower electrode 38b by means of a conducting line 28, and electrodes 38a and 40b are connected to an electrical circuit by means of conducting lines 27 and 29, respectively, the electrical circuit including a switching element. Such configuration provides an anti-parallel connection of the electrodes, wherein the switching element functions as an on/off switch, thereby alternately increasing the mechanical impedance of layer 2.

Figure 7C:
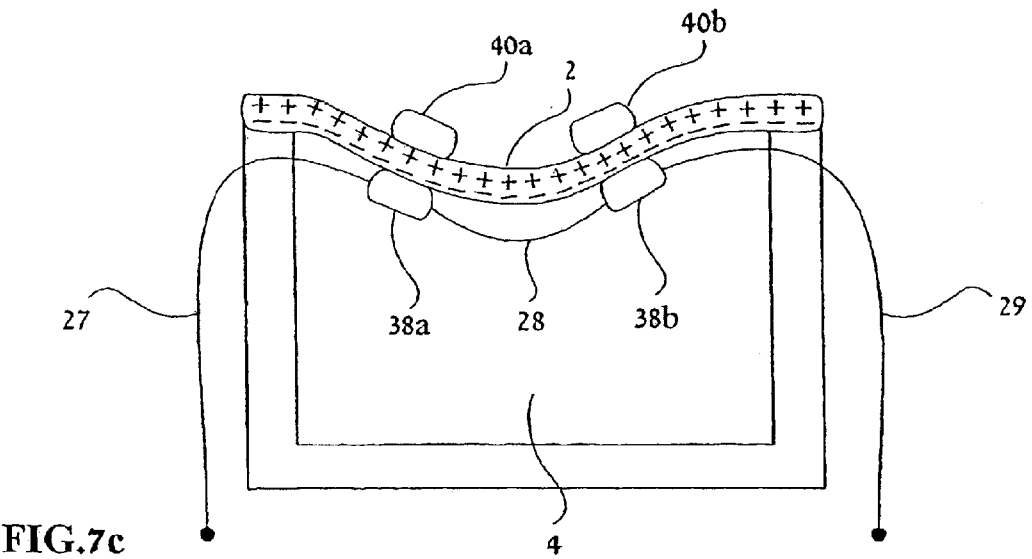

In order to reduce the complexity of the electrical connections, layer 2 may be depolarized and then repolarized at specific regions thereof. As shown in FIG. 7c, the polarity of the portion of layer 2 received between electrodes 40a and 38a is opposite to the polarity of the portion of layer 2 received between electrodes 40b and 38b. An anti-parallel connection is thus achieved by interconnecting electrodes 38a and 38b by means of a conducting line 28, and providing conducting lines 27 and 29 connected to electrodes 40a and 40b, respectively, the conducting lines for connection to an electrical circuit including a switching element.

According to another embodiment, the transmitting element includes a plurality of transducing cell members, such that the mechanical impedance of layer 2 controllably changed by appropriately interconnecting the cell members.

Figure 7D:
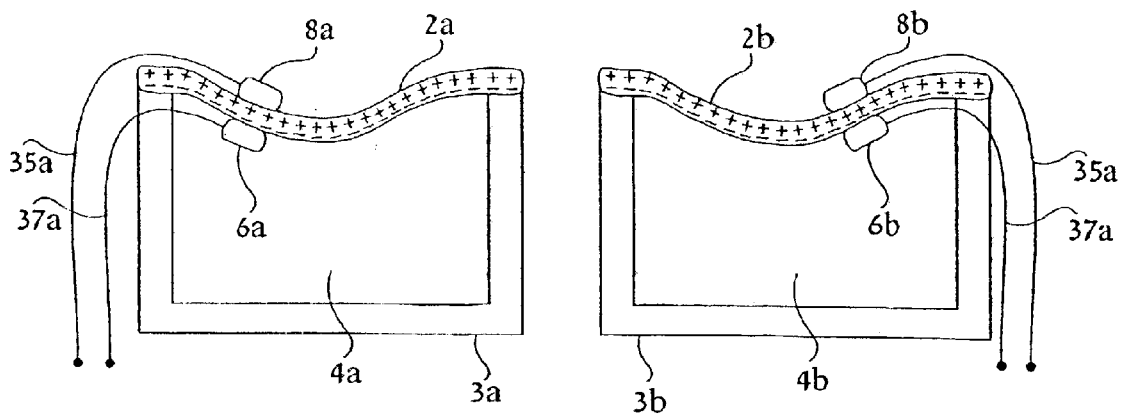

As shown in FIG. 7d, a first transducing cell member 3a including a layer 2a and a cavity 4a, and a second transducing cell member 3b including a layer 2b and a cavity 4b are preferably contained within the same substrate; and layers 2a and 2b are preferably integrally made (not shown). A first pair of electrodes including electrodes 6a and 8a is attached to layer 2, and a second pair of electrode including electrodes 6b and 8b is attached to layer 2b. Electrodes 6a, 8a, 6b and 8b are electrically connected to an electrical circuit by means of conducting lines 37a, 35a, 37b and 35b, respectively, the electrical circuit including a switching element so as to alternately switch the electrical connections of conducting lines 37a, 35a, 37b and 35b so as to alternately provide parallel and anti-parallel connections, substantially as described for FIG. 7a, thereby alternately decreasing and increasing the mechanical impedance of layers 2a and 2b.

Figure 7E:
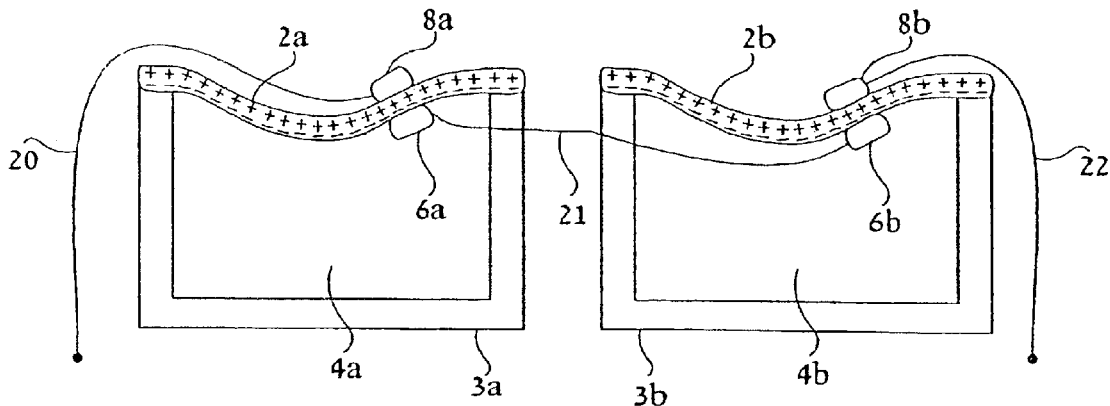

FIG. 7e illustrates another embodiment, wherein the first and second transducing cell members are interconnected by means of an anti-parallel connection. As shown in the figure, the polarity of layer 2a is opposite to the polarity of layer 2b so as to reduce the complexity of the electrical connections between cell members 3a and 3b. Thus, electrode 6a is connected to electrode 6b by means of a conducting line 21, and electrodes 8a and 8b are provided with conducting lines 20 and 22, respectively, for connection to an electrical circuit including a switching element, wherein the switching element preferably functions as an on/off switch so as to alternately increase the mechanical impedance of layers 2a and 2b.

Figure 7F:
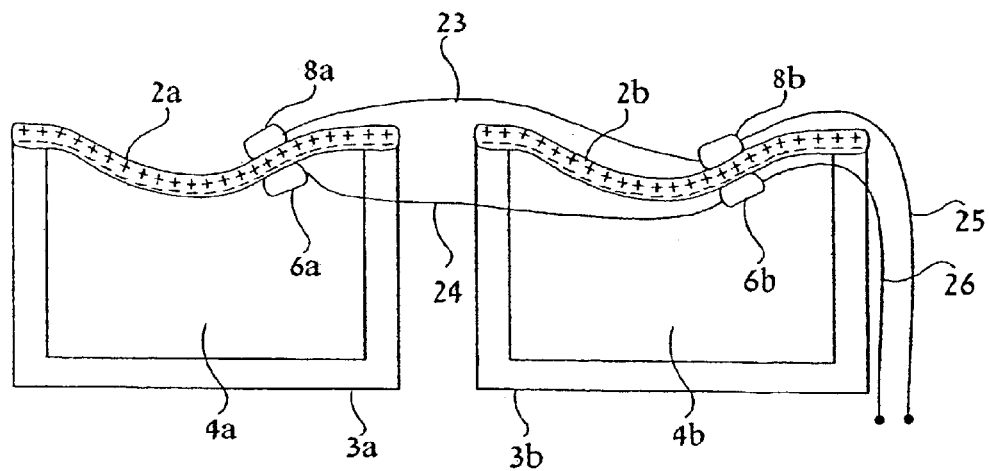

FIG. 7f shows another embodiment, wherein the first and second transducing cell members are interconnected by means of a parallel connection. As shown, electrodes 6a and 6b are interconnected by means of conducting line 24, electrodes 8a and 8b are interconnected by means of conducting line 23, and electrodes 6b and 8b are provided with conducting lines 26 and 25, respectively, the conducting lines for connection to an electrical circuit including a switching element. The switching element preferably functions as an on/off switch for alternately decreasing and increasing the mechanical impedance of layers 2a and 2b.

Figure 8:
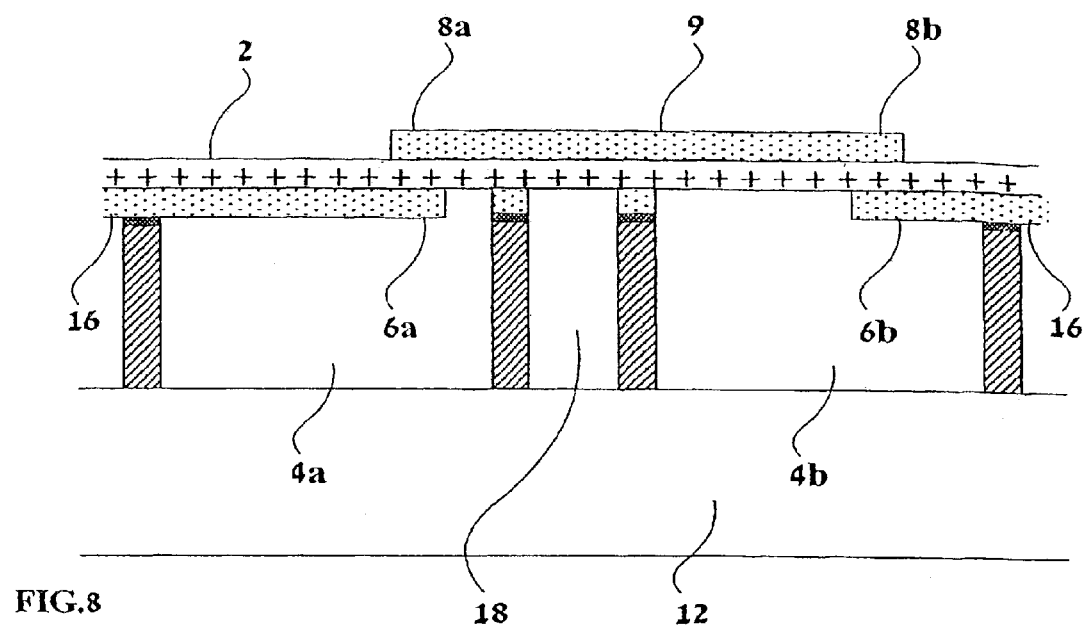
FIG. 8 is a longitudinal section of a transmitter element according to the present invention including an anti-parallel electrical connection.

FIG. 8 shows a possible configuration of two transducing cell members etched onto the same substrate and interconnected by means of an anti-parallel connection. As shown in the figure, the transducing cell members are covered by a common piezoelectric layer 2, wherein the polarity of the portion of layer 2 received between electrodes 6a and 8a is opposite to the polarity of the portion of layer 2 received between electrodes 6b and 8b. Electrodes 8a and 8b are bonded by means of a conducting line 9, and electrodes 6a and 6b are provided with conducting lines 16 for connection to an electrical circuit.

Figure 9:
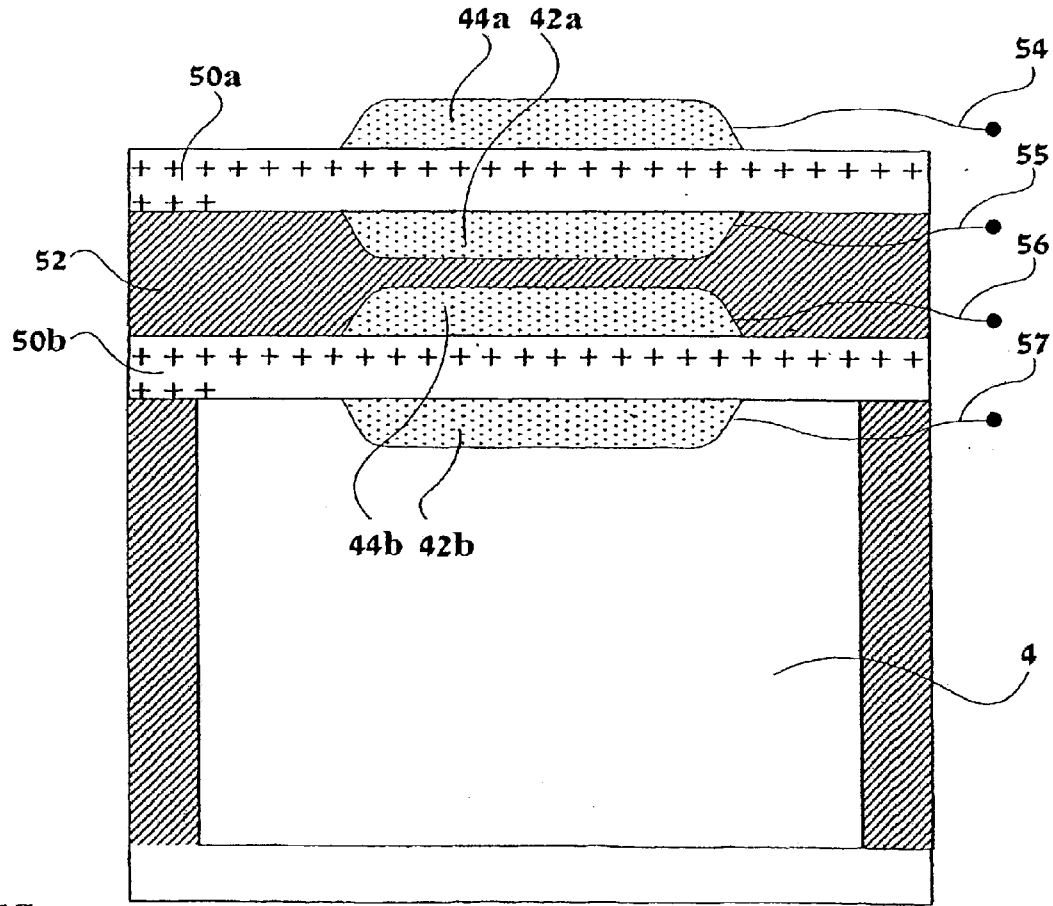
FIG. 9 is a longitudinal section of another embodiment of a transmitter element according to the present invention.

Another embodiment of a transmitter element according to the present invention is shown in FIG. 9. The transmitter element includes a transducing cell member having a cavity 4 covered by a first and second piezoelectric layers, 50a and 50b, preferably having opposite polarities. Preferably, layers 50a and 50b are interconnected by means of an insulating layer 52. Attached to layer 50a are upper and lower electrodes 44a and 42a, and attached to layer 50b are upper and lower electrodes 44b and 42b. Electrodes 44a, 42a, 44b and 42b are provided with conducting lines 54, 55, 56 and 57, respectively, for connection to an electrical circuit.

It will be appreciated that the above descriptions are intended only to serve as examples, and that many other embodiments are possible within the spirit and the scope of the present invention.

What is claimed is:

1. A transducer element, comprising:
   (a) a cell member having a cavity;
   (b) a flexible piezoelectric layer attached to said cell member so as to isolate said cavity from an external medium, said cavity having a lower acoustic impedance than said external medium, said piezoelectric layer having an external surface and an internal surface, and
   (c) a first electrode attached to said external surface and a second electrode attached to said internal surface.

2. The transducer element of claim 1, wherein said cell member comprises a substrate, and said cavity is etched into said substrate.

3. The transducer element of claim 2, where said substrate includes an electrically insulating layer and an electrically conducting layer.

4. The transducer element of claim 3, wherein said first electrode is integrally made with a substantially thin electrically conducting layer disposed on said substrate.

5. The transducer element of claim 4, wherein said substantially thin electrically conducting layer is connected to said substrate by means of a sealing connection.

6. The transducer element of claim 2, wherein said substrate includes a plurality of cell members.

7. The transducer element of claim 6, wherein said plurality of cell members are electrically connected in parallel connections.

8. The transducer element of claim 6, wherein said plurality of cell members are electrically connected in serial connections.

9. The transducer element of claim 1, wherein said cell member is circular in shape.

10. The transducer element of claim 1, wherein said cavity includes gas.

11. The transducer element of claim 10, wherein said gas is of substantially low pressure.

12. The transducer element of claim 1, wherein said transducer element is used as a transmitter.

13. The transducer element of claim 12, further including a switching element electrically connected thereto so as to controllably change the mechanical impedance of said piezoelectric layer.

14. A transmitter element comprising:

a cell member having a cavity;

a flexible piezoelectric layer attached to said cell member, said piezoelectric layer having an external surface and an internal surface; and a first electrode attached to said external surface and a second electrode attached to said internal surface, said electrodes coupled to an electrical circuit, said electrical circuit having a switching element, whereby a switching frequency of said switching element controls the mechanical impedance of the piezoelectric layer, wherein the switching frequency of said switching element equals the frequency of an electrical message signal arriving from an electric member.

15. The transmitter element of claim 17, wherein said electronic member is a sensor.

16. A transmitter element comprising:

a cell member having a cavity:

a flexible piezoelectric layer attached to said cell member, said piezoelectric layer having an external surface and an internal surface, and a first electrode attached to said external surface and a second electrode attached to said internal surface, said electrodes coupled to an electrical circuit, said electrical circuit having a switching element, whereby a switching frequency of said switching element controls the mechanical impedance of the piezoelectric layer, wherein said switching element is for modulating a reflected acoustic wave according to a message signal arriving from an electronic component.

* * * * *